(12) United States Patent
Sliwa et al.

(10) Patent No.: US 9,445,211 B2
(45) Date of Patent: Sep. 13, 2016

(54) METHODS FOR MANUFACTURING HIGH INTENSITY ULTRASOUND TRANSDUCERS

(75) Inventors: Jack Sliwa, Los Altos, CA (US); Jonathan L. Podmore, San Carlos, CA (US); Chris Bagley, Santa Clara, CA (US); John E. Crowe, Menlo Park, CA (US); Michael Holzbaur, East Palo Alto, CA (US); Derek Hillstrom, Union City, CA (US); Steve Schellenberg, Aptos, CA (US); Peter Goetz, Aptos, CA (US); Stephen A. Morse, Menlo Park, CA (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 3747 days.

(21) Appl. No.: 11/104,294

(22) Filed: Apr. 11, 2005

(65) Prior Publication Data
US 2006/0236525 A1 Oct. 26, 2006

(51) Int. Cl.
*H04R 31/00* (2006.01)
*H03H 3/02* (2006.01)
*H03H 3/04* (2006.01)
*H03H 3/08* (2006.01)
*B06B 1/06* (2006.01)

(52) U.S. Cl.
CPC ................ *H04R 31/00* (2013.01); *B06B 1/06* (2013.01); *H03H 3/02* (2013.01); *H03H 3/04* (2013.01); *H03H 3/08* (2013.01); *H03H 2003/045* (2013.01); *H03H 2003/0407* (2013.01); *Y10T 29/42* (2015.01); *Y10T 29/49004* (2015.01); *Y10T 29/49005* (2015.01)

(58) Field of Classification Search
CPC ............ H04R 1/00; B06B 1/06; H03H 3/02; H03H 3/04; H03H 3/08; H03H 2003/0407; H03H 2003/045; Y10T 29/42; Y10T 29/49004; Y10T 29/49005
USPC ....... 29/594, 25.35, 846, 842; 310/312, 322, 310/326, 324; 343/738; 601/4; 324/639
See application file for complete search history.

(56) References Cited

U.S. PATENT DOCUMENTS

| 3,736,632 | A | * | 6/1973 | Barrow ...................... 29/25.35 |
| 4,562,370 | A | | 12/1985 | Von Dach |
| 4,823,773 | A | * | 4/1989 | Naser et al. ...................... 601/4 |
| 5,389,848 | A | * | 2/1995 | Trzaskos ...................... 310/322 |
| 5,780,713 | A | | 7/1998 | Ruby |
| 5,815,900 | A | | 10/1998 | Ichikawa et al. |
| 5,855,049 | A | | 1/1999 | Corbett, III et al. |

(Continued)

FOREIGN PATENT DOCUMENTS

| JP | 62242404 A | * | 10/1987 | ............... 29/25.35 X |
| JP | 02074888 A | * | 3/1990 | .................... 343/738 |

OTHER PUBLICATIONS

English Language Translation of Japanese Patent Publication, JP 2-74888.*

*Primary Examiner* — A. Dexter Tugbang
(74) *Attorney, Agent, or Firm* — Wiley Rein LLP (57) ABSTRACT

A method of manufacturing an ultrasound transducer is provided. The ultrasound transducer is activated and the activity across the transducer is measured to determine whether the activity at any area does not meet an acceptance criteria. The transducer is then modified so that the area meets the acceptance criteria. The transducer may be modified with a laser which removes material from the area which does not meet the acceptance criteria.

27 Claims, 6 Drawing Sheets

(56) References Cited

U.S. PATENT DOCUMENTS

| | | | |
|---|---|---|---|
| 5,873,153 A * | 2/1999 | Ruby et al. | 29/25.35 |
| 6,036,648 A | 3/2000 | White et al. | |
| 6,308,571 B1 * | 10/2001 | Stanish et al. | 324/639 X |
| 6,515,402 B2 * | 2/2003 | Klee et al. | 310/324 |
| 6,760,960 B2 | 7/2004 | Sakaguchi et al. | |
| 6,805,129 B1 | 10/2004 | Pless et al. | |
| 6,840,936 B2 | 1/2005 | Sliwa et al. | |
| 2004/0049902 A1 | 3/2004 | Nguyen | |

* cited by examiner

METHODS FOR MANUFACTURING HIGH INTENSITY ULTRASOUND TRANSDUCERS

BACKGROUND

The present invention is directed to ultrasound transducers and their methods of manufacture and use.

In some applications of ultrasound transducers, such as high-intensity ultrasound therapeutic devices, the ultrasound transducers may have to meet certain criteria regarding the distribution of activity across the ultrasound transducer. For example, it may be desirable to provide acoustic or thermal uniformity across the proximate ultrasound transducer face as well as in the distal transducer's focal region. One reason for requiring acoustic or thermal uniformity proximately at the transducer face is that some of these devices also provide therapy in the nearfield and may have to avoid localized hot spots which can lead to overheating of nearfield tissue portions. Another reason to provide acoustic and thermal nearfield uniformity is that some ultrasound devices may utilize water-filled contact members which can undergo undesirable localized boiling if hot spots are present. Such considerations are in addition to the normal expectation of acoustic uniformity at the distal focus-which would lead to thermal-heating uniformity at that distal focus. As practitioners of the acoustic arts know, acoustic output nonuniformities on the proximate transducer face will also cause nonuniformities at the focus. Various examples of such devices are found in U.S. Pat. Nos. 6,840,936 and 6,805,129 which are hereby incorporated by reference.

The present invention is also directed to methods and devices for manufacturing ultrasound transducers and to methods for modifying the characteristics of an ultrasound transducer. The acceptance criteria regarding the distribution of activity across the ultrasound transducer nearfield, farfield or focal region typically require that some transducers be rejected. The present invention provides devices and methods for modifying transducers which might otherwise be rejected or might perform less than optimally. The present invention also allows for a substantial speedup in the process of determining whether such uniformity is acceptable or is a candidate for our additional and optional inventive uniformity-correction methods.

SUMMARY

The present invention provides methods and devices for modifying an ultrasound transducer. In accordance with a method of the present invention, an ultrasound transducer is activated and then the activity across the transducer is measured to determine whether any parts of the transducer do not meet an acceptable activity level. For example, if the activity level exceeds a threshold level, the transducer is then modified to reduce the activity level at the portion which exceeds the acceptance criteria. The present invention may also be used to modify a transducer having unacceptable low activity but is particularly useful in modifying areas of unacceptably high activity. Most frequently the activity is acoustic activity whose presence, as explained below, can be monitored using thermographic activity-monitoring or imaging means or using hydrophone or Schlieren imaging means.

The transducer may be modified in a number of different ways to favorably change or alter the distribution of activity across the transducer such as by removing material from the transducer. The material may be removed from an acoustically active material or from an acoustically inactive or passive material such as an electrode or matching layer. Material may be removed with a laser, a mechanical abrasion device or any other suitable material removal device including those which use erosion, etching, abrasion or ablation. The transducer may also be modified by changing the dimensions of the transducer, by selective poling/depoling of a piezomaterial or by even adding material to the transducer. The transducer may be retested after such modification and modified again if necessary. It should be understood that any or all of these modification measures are undertaken in response to a uniformity test indicating an undesirable uniformity different from an expected desired uniformity. Thus our invention is fundamentally different than any method used to create fixed predefined activity patterns in a transducer such as by patterning a transducer electrode during manufacturing with a fixed mask in order to achieve well-known acoustic apodization profiles. Such measures have nothing to do with responding to an undesired and varying nonuniformity appearing in random locations as does our invention.

The present invention is also directed to a system for modifying an ultrasound transducer. The system includes a sensor for sensing the activity across the ultrasound transducer and a modifying apparatus for modifying the transducer. A memory element may also be used to temporarily or permanently save at least one partial map of the activity across the transducer. It will be understood by the reader that a nonuniformity "across" the transducer may contribute to undesired nonuniform performance in the proximal transducer-face and/or distal transducer-focus regions. In either or both cases the invention provides beneficial modification capabilities.

These and other aspects of the invention will become apparent from the following description, drawings and claims.

DESCRIPTION OF THE PREFERRED EMBODIMENTS

Figure 1:
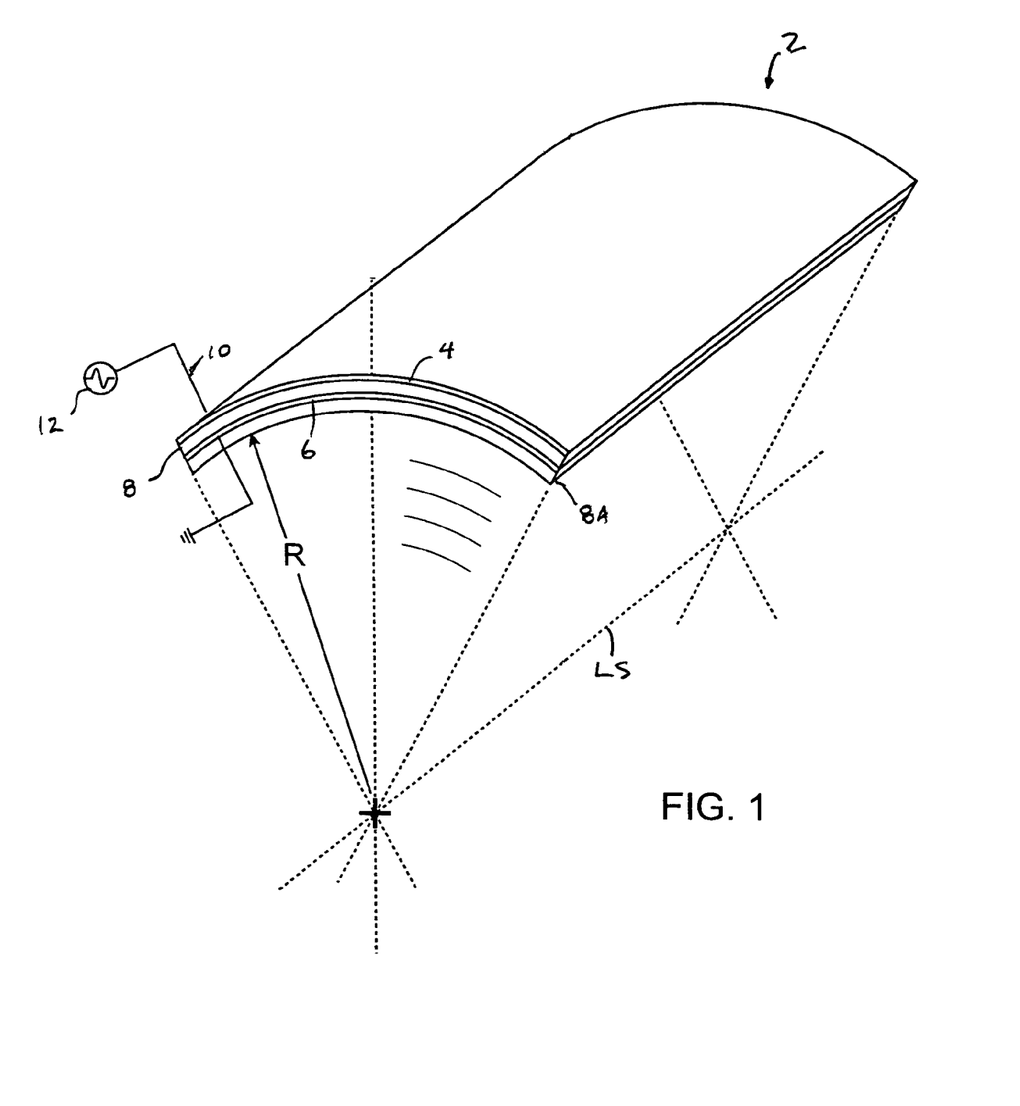
FIG. 1 is a perspective view of an ultrasound transducer showing its layers and focal geometry
Figure 2:
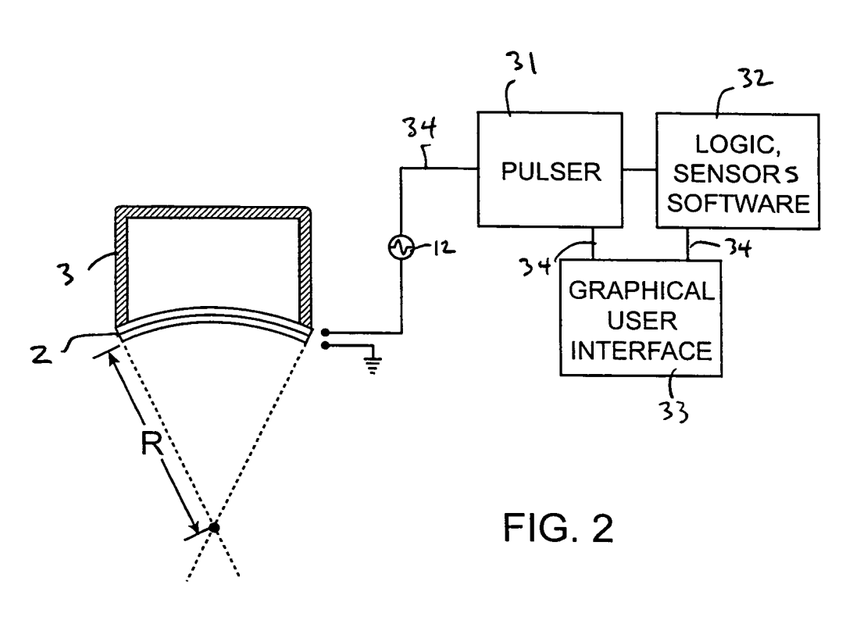
FIG. 2 is a view of the transducer with a schematic view of a therapy apparatus.

Referring to FIGS. 1 and 2, an ultrasound transducer 2 is shown. The ultrasound transducer 2 generally has a piezoelectric layer 8 and one or more acoustic matching layers 8A. Typically, the piezoelectric layer 8 is positioned between an active or "hot" electrode 4 and a passive or "ground" electrode 6. The piezoelectric layer 8 may be made of any suitable piezoelectric material such as lead-zirconate-titanate (PZT), lead metaniobate, lithium-niobate or polyvinylidifluoride (PVDF) compounds as is known. Of course, any other suitable material may be used including those made of piezoceramics, piezopolymers, electrostrictive materials and magnetostrictive materials. The piezoelectric layer 8, matching layer 8A, and electrodes 4, 6 may be laminated or bonded in any suitable manner such as by known epoxy lamination. Electrodes 4, 6 may be provided in any suitable manner such as by depositing or laminating a metal film or foil on or to the piezomaterial and matching layer. In some cases the matching layer 8a will comprise electrically conductive material and it may then itself also serve as the electrode 6.

The active transducer electrode 4 has an associated electrical lead 10 coupled to a power source 12 for driving the ultrasound transducer 2 in a conventional manner. The ultrasound transducer 2 of FIGS. 1 and 2 is cylindrically curved so that the ultrasound energy is focused and, in particular, cylindrically focused along a linear focal-line segment LS. The focal length of the ultrasound energy is essentially the radius of curvature R of the ultrasound transducer 2. The present invention may be particularly useful in modifying transducers 2 having a focal length less than 12 mm and even less than 10 mm. The present invention is particularly useful in that one may modify the transducer proximal-face uniformity thereby improving both the nearfield treatment uniformity as well as the distal focal-line treatment uniformity. For example, if the transducer 2 were a HIFU lesion-making transducer having a focal radius of 8 or 10 mm one could modify the transducer 2 uniformity using the invention such that the HIFU treatment uniformity is improved both in the nearfield and in the farfield. In that manner a uniform tissue lesion can be formed everywhere between the distal focal line LS and the proximal tissue surface transducer-face.

FIG. 2 schematically shows the transducer 2 of FIG. 1 mounted to a transducer housing 3. An electrical pulser subsystem 31, a group of logic, sensors and software 32 and a graphical user interface 33 are connected to each other and to the transducer 2 by wires, cables or data buses 34. In this particular transducer application the transducer 2 is air-backed as shown. This is a common measure for HIFU transducers in order not to generate large amounts of waste heat. The "pulser" 31 typically delivers continuous wave (CW) pulses or pulsetrains at an operating frequency of 1-10 megahertz for the most common HIFU applications. The graphical user interface keeps the user informed of delivered power levels and temperatures etc while the logic/sensors/software portion typically includes interlocks, system control software and patient information inputs. It will be noted in both FIGS. 1 and 2 that the driven "hot" lead 10 connected to the energy source 12 applies the excitation energization across the piezomaterial thickness in reference to an opposed ground electrode.

Figure 3A:
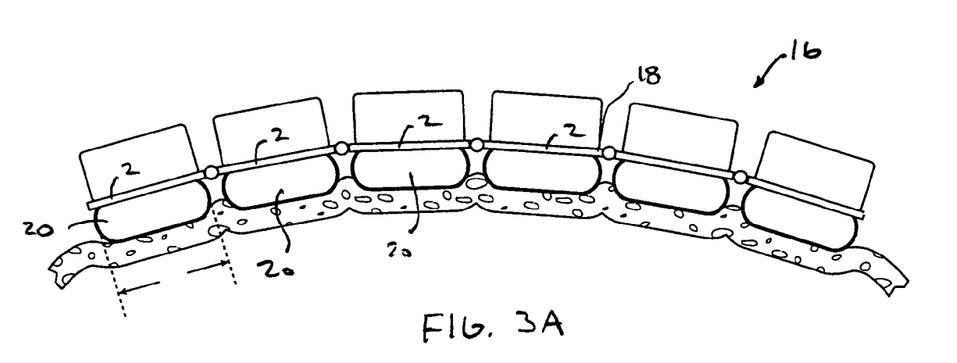
FIG. 3A shows a medical device using a number of ultrasound transducers.
Figure 3B:
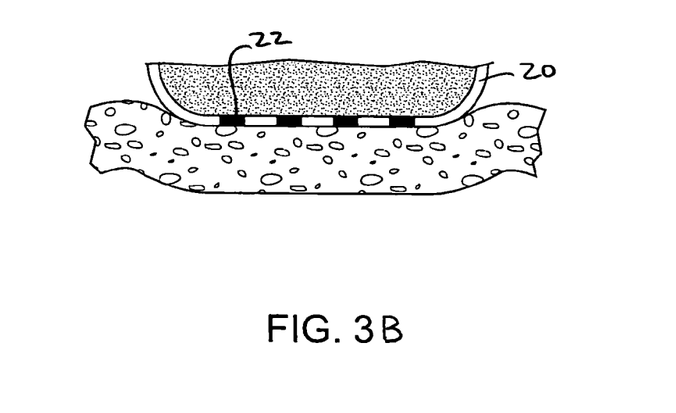
FIG. 3B shows a membrane in contact with tissue being treated.

The ultrasound transducer 2 may be mounted to a medical device 16 as shown in FIGS. 3A and 3B which is used to ablate myocardial tissue in the manner described in the patents incorporated herein by reference. A number of ultrasound transducers 2 are mounted on a body 18 and the body is able to form a closed loop around a structure such as the heart. Of course, the present invention may be used in any suitable procedure and, furthermore, the ultrasound transducer 2 is merely one example of an ultrasound transducer 2 to which the present application may be applied. Referring to FIG. 3B, the ultrasound transducer 2 may have a fluid filled membrane 20 which acts as the contact surface to the tissue and may also provide cooling. The fluid, such as saline, is delivered to the membrane 20 and may either circulate in a closed loop and/or may weep out holes 22 in the bottom of the membrane 20 as described in the patents which have been incorporated herein by reference. As mentioned above, the present invention is directed to modifying the characteristics of the ultrasound transducer 2 such as the elimination of local hot spots which may cause overheating of the nearfield tissue or excessive heating or boiling of the nearfield juxtaposed fluid. Localized boiling can cause obvious problems including reduction, redirection or reflection of propagating ultrasound energy and subsequent undesired nonoptimal treatment to tissue. Further, any nonuniformity on the transducer face may result in a nonuniformity at the focal line(s) LS and certainly, at-least, in nonuniformities in the acoustic beam between the transducer face and the distal focal line(s) LS.

Depending on the particular device being manufactured, the acceptance criteria for the activity level across the ultrasound transducer 2 proximal face may vary depending on the nearfield, focal and farfield uniformity requirements. For example, it may be desirable to have uniform acoustic energy or heat generation take place in nearby proximal tissue. The "activity" across the transducer face 2 is a direct or indirect measure of an acoustic parameter such as acoustic intensity output, acoustic-receive sensitivity or acoustically output-derived waste-heat (which correlates with acoustic output). Note here that the modification may be applied to transducer energy output as for delivering a HIFU therapy or may be applied to a transducer energy input as for an acoustic receive-mode uniformity. Thus the invention is applicable to both outgoing and incoming energy uniformities. Of course, it may also be desired to have a controlled non-uniform distribution of output energy (or receive-sensitivity) activity across the ultrasound transducer as opposed to a uniform activity. In any event the invention can correct unexpected deviations from any desired uniformity pattern. The acceptance criteria may be an absolute set level of activity or may simply comprise a relative comparison of one part of the transducer with another part of the transducer or to the transducer as a whole. Furthermore, the transducer 2 may be activated at a power which is lower than would be expected during operation so that the threshold criteria could, in fact, be a lower level of activity than expected during actual use. Low power testing may be used so long as the acceptance criteria is relevant for the power used during testing. Thus, the acceptance criteria may be much different than the desired full-power operating limits of the ultrasound transducer but usefully predictive.

Figure 4:
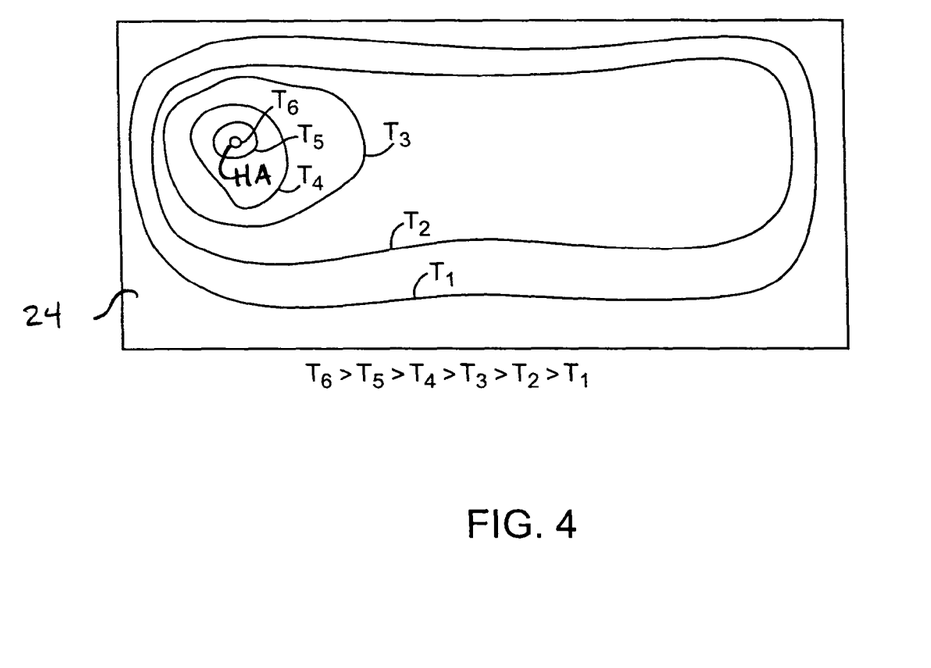
FIG. 4 shows a map of activity across the transducer.

The ultrasound transducer 2 is tested by activating the transducer 2 and sensing a parameter related to the transducer activity across all or part of the ultrasound transducer 2-typically in the nearfield, as that is where any corrective modifications can be physically made as will be discussed. Referring to FIG. 4, a map 24 of the activity across the ultrasound transducer 2 output face (as seen from the exposed matching layer 8a surface) is shown. The map 24 may be an "indirect" thermal map of acoustically-derived waste-heat or a "direct" map of acoustic activity such as an acoustic intensity. The map 24 shown in FIG. 4 has a high activity area HA which does not meet the acceptance criteria or threshold level of activity. As discussed above, the high activity area HA might produce localized boiling or excessive heating of the tissue in the near of farfields. As can be appreciated, the map 24 of FIG. 4 may also depict acoustic activity across the ultrasound transducer with the HA being an area where high acoustic activity is measured. Furthermore, the map 24 may be a steady-state map or a transient state map. The map may include lines of activity or temperature such as isotherms as shown or may comprise an array of values. Transient isotherms of temperature are particularly telling of acoustic output nonuniformities. Typically, the transient delay involved is a characteristic of the structure and comprises a thermal diffusion time constant measured in milliseconds to seconds. Short transient mapping allows for inspection at very low total inputted (pulsed) power such that the transducer optionally need not be coupled to the patient or to water during such testing.

The term "activating" as used herein in reference to the transducer may mean applying an activation excitation energy or field such that acoustic energy is produced by the transducer. As used herein, "activity" may mean any characteristic of the acoustic energy produced by the transducer measured directly or indirectly as described herein. "Activating" the transducer may also mean using the transducer to receive acoustic energy which is transduced into electrical impulses. The "activity" of the transducer in this case would be the electrical impulses. Thus, the transducer may be "activated" to transduce an excitation energy or field into acoustic energy or may be "activated" to transduce acoustic energy into electrical impulses.

The map 24 of the activity of the ultrasound transducer 2 may be created directly or indirectly in any suitable manner. For example, the map 24 may be acquired by progressive or rastered hydrophone scanning using known single or arrayed hydrophones, using Schlieren-imaging, or using actual ablation of a tissue or other thermal-witness or acoustic-witness phantom such as known albumin-containing phantoms. The thermal map 24 may be acquired by thermography or by the heating of a juxtaposed exposure phantom. Of course, other measures of the activity across the ultrasound transducer 2 may be used to determine whether higher than acceptable activity exists when the transducer 2 is activated. The term "map" as used herein may have one, two or even three dimensions. The map 24 of FIG. 4 may be a transient pulsed temperature map which is two-dimensional (three dimensional if you account from the curved surface being imaged using thermography). The map 24 could be one dimensional when measured along the focal line of FIG. 1 or could be a three dimensional map when using 3D Schlieren imaging. The term "map" may, of course, also simply be a listing of numerical values related to the activity corresponding to a particular area or location on the transducer 2. The term "area of the transducer" as used herein may also have one, two or three dimensions in keeping with the term "map" as defined herein since the map of the area across the transducer may have one, two or three dimensions.

It is understood that the use of a saved or stored map 24 may not strictly be necessary since one could progressively image or sense the activity across the transducer 2 and simultaneously modify the transducer as described herein in a piecemeal manner. However, in preferred embodiments at-least a partial map is obtained before any modification is carried out since the map allows for corrections to be made to normalized criteria as well as to absolute criteria. Thus, inspection typically involves at-least a partial map of activity being sampled along a 1D or 2D line or surface. This line or surface may be sampled proximal to the transducer face or distally near or at the transducer focus or at any other region of the beam. The line or surface may have any orientation with respect to the transducer and may comprise one or more such lines or surfaces thereby forming a surface or volume of sampling. In FIG. 4 we show a thermal map of the transducer face itself as fired into air using a very short CW pulse such that peak heating within the milliseconds to few-seconds timeframe is on the order of 1 to 50 degrees C. The "map" may also comprise a mathematically processed set of data-such as an averaged map taken over several separate heating events. Thus, the activity of the transducer 2 may be determined directly or indirectly in a number of different manners without departing from the scope of the invention. In all cases deviations being looked for are deviations from an intended map-even if the intended map is a usefully "shaped" nonuniform map.

Figure 5:
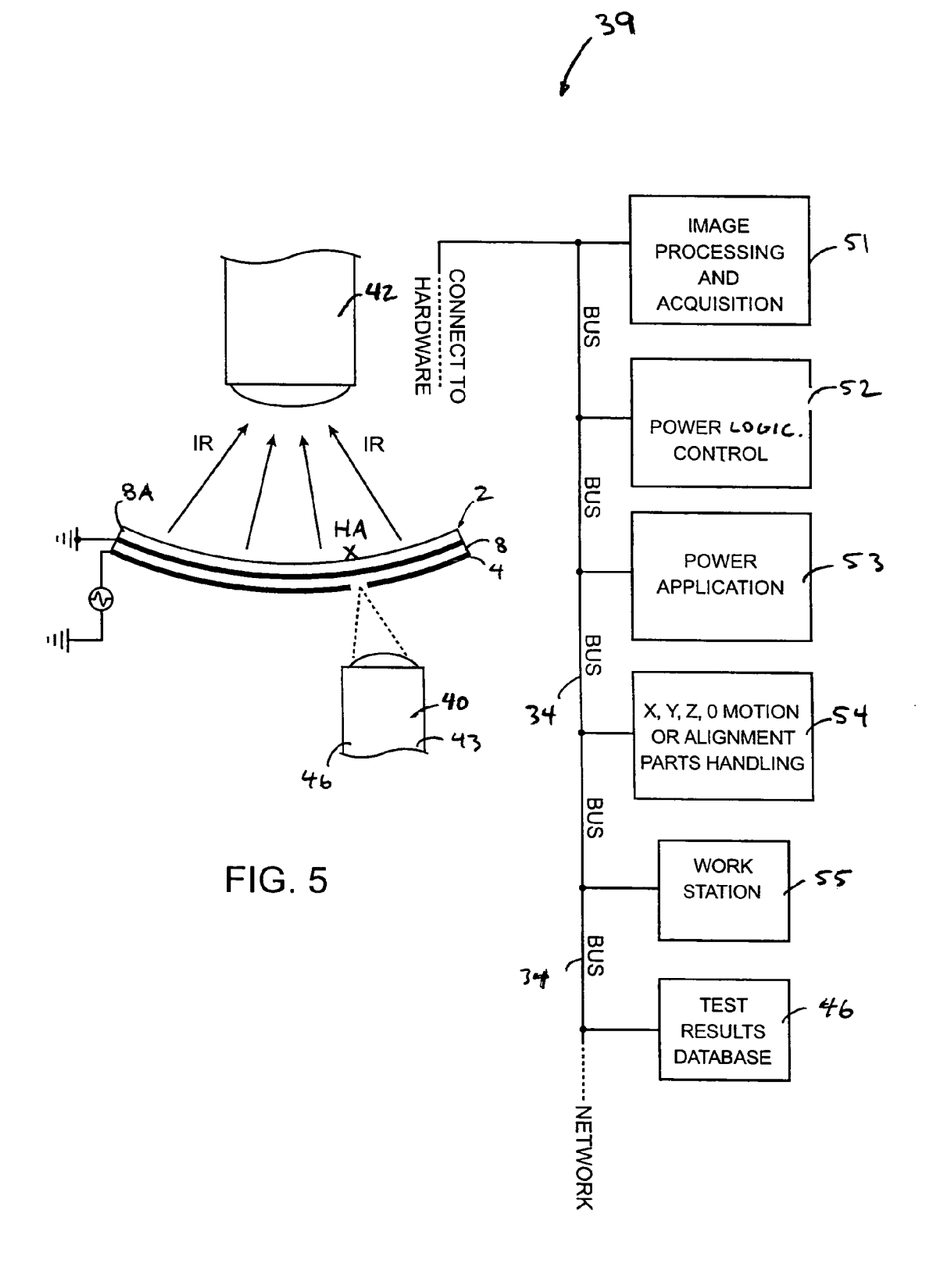
FIG. 5 shows a system for modifying an ultrasound transducer in accordance with the present invention.

Referring to FIG. 5, the ultrasound transducer 2 may be tested and modified with a system 39 which includes a modifying apparatus 40. The apparatus 40 may modify the transducer 2 immediately after evaluating the activity across the ultrasound transducer 2 or may use the map 24 as discussed above to do so at a later point in time. To this end, the system 39 may include an activity sensor 42 which detects the level of activity across the transducer 2 preferably in a high speed serial or even more preferably in a rapid parallel manner. The sensor 42 may be an acoustic sensor, a thermal sensor or another type of sensor which detects the activity level across the transducer 2. The system 39 may simultaneously or sequentially acquire the acoustic or thermal map 24 and then perform modification of the transducer 2 to improve or correct that map without requiring transfer of the transducer 2 to another test apparatus. Of course, the distribution of activity across the ultrasound transducer 2 may be saved as the map 24 so that the ultrasound transducer 2 may be moved from the sensor 42 to a separate modifying device 40. (40 not shown as being separate in FIG. 5). The system 39 may also include a memory element 46, which may be part of the modifying device 40 or sensor 42, which saves the map 24 of activity created by the sensor 42 for use by the modifying apparatus 40. The system 39 may also receive a number of maps 24 of different regions of the transducer 2 or may receive a number of maps 24 related to different parameters. It is also understood that the transducer 2 may be directly measured in the manner described herein or another suitable manner. The activity across the transducer 2 may also be detected indirectly by sensing activity in ultrasound beam in any suitable manner including some of those described herein related to detecting acoustic activity. Memory means, such as 46, may not only store inspection maps but may also store the desired (perfect part) maps to which tested parts are compared. As is known in the arts of product inspection, the desired maps may include acceptance tolerances of an absolute or comparative nature.

The modifying apparatus 40 may be used to modify the distribution of activity across the ultrasound transducer 2 in any suitable manner at one or more locations. We note that in FIG. 5 the modifying apparatus operates upon the exposed backside of the piezomaterial/electrode 8/4. This is because in this example we wish to directly modify the acoustics producing member (the electroded PZT) in order to modify output. FIG. 5 illustrates that mapping is taking place from the frontside or matching-layer 8a side. More or less, the acoustic nonuniformities in the piezolayer 8 appear as hotspots on the overlying matching layer 8a outer surface-particularly for short pulse times and thermally insulative and attenuative matching layer materials. We include in the scope of the invention practicing both mapping and modification from the same side-such as from the backside electrode 4 side as well as from or on opposite sides. The advantage of this is that the thermal contrast of hot spots is maximal here where you are not "looking through" a matching layer.

The modifying device 40 may be an excimer laser 43 which is used to destroy or otherwise modify part of an area of high activity. UV lasers and excimer lasers may be used since they are capable of nonthermal removal of thin films without underlying thermal substrate damage. Use of such an excimer laser 43 would allow for the selective removal of electrode material from an optically exposed electrodes 4 without damaging the underlying piezoelectric layer 8. By removing an electrode portion the energization bias is no longer applied to the PZT in the removed region. Another method of modifying the ultrasound transducer is to remove electrode or acoustic-component material with the modifying apparatus 40 being a microabrasive device which mechanically removes material. If the transducer 2 is curved as shown in FIGS. 1, 2 and 5 the transducer 2 and/or the laser 43 may be manipulated so that the beam impacts the electrode at a desired illumination angle such as 90 degrees. One may optically or thermally optimize one or both of the electrodes 4, 6 to have appropriate absorbance or reflectivity in addition to having the required electrical and metallurgical properties to accept solder or other connections as necessary for the particular application and materials being used. One may also optimize a material making up the piezocomponent 8 or matching layer(s) 8a such that it is easily and controllably modified by modification tool 40.

Referring to FIG. 5, the high activity area HA is easily modified by removing or damaging a portion of electrode 4 opposite the overactive region HA. The portion of the electrode 4 (or electrode 6 if it is accessible to modification) that is modified may be at the high activity area HA as shown in FIG. 5 or may be near or around the high activity area so long as the result is to lower the activity in the high activity area HA. The mapping and modifying apparatus 39 may include an image acquisition and processing device 51 which acquires and processes the inspection map 24 relative to a desired map. The apparatus 39 may also include powering, logic and control device 52 and a transducer power application supply 53. Still another device 54 may be used to perform needed motion or alignment of the transducer relative to the modifying apparatus and/or inspection means 42. A user interface provided by a workstation or terminal 55 is used to control the devices and provide information to the user. The test results may also be saved in a database 46. The various components are coupled together with bus and cable connections 34 and uploaded to a network. The description of the mapping and modifying apparatus 39 is merely one example of an apparatus which may be used to modify the transducer 2 and it can be appreciated that numerous other devices may be used to modify transducers without departing from the scope of the present invention. More explicitly we note that some or all of the systems 39 functions or memory may be network-resident in that, for example, a network provides most or all required storage of desired and measured activity maps for example. In another variation the mapping and modification apparatus 39 may be able to hold several transducers 2 which can sequentially or simultaneously at-least one of be mapped or modified without transfer of the transducers under test. An excellent example of this would be a system 39 wherein a thermographic imager 43 maps an entire tray of 50 transducers. Another variation would be where virtual instruments, such as software, allow for a conventional PC to operate one or more test and modification tools.

The ultrasound transducer 2 may be modified in a number of different ways but what they all have in common is that an acoustic activity parameter relating to the transducers function or acoustic beam will be beneficially directly or indirectly modified at least one physical location. This location is typically on or at the transducer but could also be, for example, in an acoustic standoff material that spaces the transducer from the workpiece or patient and through or across which acoustic energy is transmitted or received. The ground electrode 6 or the active electrode 4 may be altered at areas of activity not meeting the acceptance criteria, such as regions of unacceptably high activity, using the laser 43 or the like-give modification access. In one embodiment, for example, the activity sensor 42 performs an image-wise thermography test and electrode material is removed as necessary such as with the laser 43 in order to reduce the acoustic (and thermal) hotspot. The thermography test may be conducted on one side, such as the output matching-layer frontside or active side of the transducer 2, while the material is removed from the other side of the transducer 2 as shown in FIG. 5. This dual-side approach allows plenty of room for the mapping and modification apparatus and any motions they need to undergo.

We note that in FIG. 5 if one were to employ thermographic imaging 42 and utilize a galvanometer-scannable modification laser 43 it would be possible to carry out the entire mapping and modification sequence with minimal or no movement of the major parts of the apparatus or of the workpiece. Mapping may be accomplished using minimal or no mapping-required movement and that modification will be done using lasers and minimal motions, if any, to retain desired laser focusing and directing. "Motion" refers to relative motion which may include moving one or more of the various portions of the apparatus and/or the transducer. Thermographic imaging cameras are routinely available as from FLIR Systems of Boston, Mass. Their S-series and Phoenix™ models offer high frame rates of up to hundreds of frames per second and high sensitivity.

Referring to FIGS. 6A to 6F, various techniques for altering the activity across a transducer 2 are shown. FIGS. 6A-6F show localized alteration of the transducer 2, such as at or near the high activity area HA, however, it is understood that the localized alteration may take place at one or more discrete locations. Furthermore, the present invention is useful in modifying the transducer 2 prior to adding the matching layers 8A. Of course, the transducer 2 may also be modified after adding the matching layer(s) 8A.

Figure 6A:
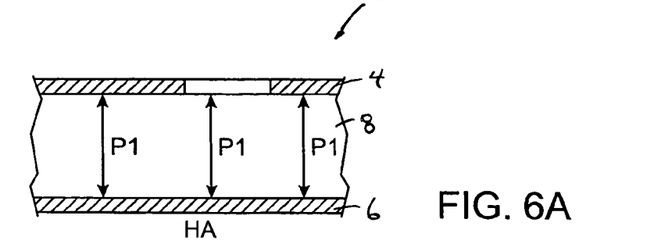
FIGS. 6A-6F are cross-sections of the ultrasound transducer after various embodiments of the inventive modifications are carried out.

Beginning with FIG. 6a we see a transducer 2 having the typical hot electrode 4 ground electrode 6, and intermediate piezomaterial such as PZT 8. This figure depicts the hotspot HA being modified by removing a portion of the hot excitation electrode 4 generally opposite the hot spot. The missing electrode 4 portion results in the region HA receiving less of a pulsed energization and thus results in reducing the local acoustic power. It should be obvious that the larger the area of removed electrode 4, the larger the region which is reduced in acoustic output intensity. The piezomaterial 8 of FIG. 6a has a uniform poling P1 which is depicted as not being altered by the electrode removal modification. This can be accomplished, as previously described, by using a nonthermal excimer laser to etch the electrode away locally.

Figure 6B:
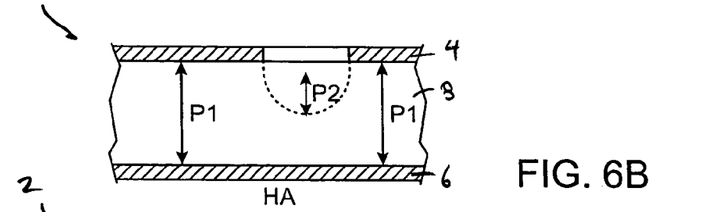

Moving now to FIG. 6b we see another transducer 2. This transducer hotspot HA has been modified. Similarly to that of FIG. 6a however note that the poling of the piezomaterial 8 beneath the etched electrode region has been reduced to P2 from its original higher level P1. This is what would happen if a thermal-based laser such as a Nd-YAG or CO2 laser is used. Such thermal-based lasers inevitable heat the PZT not only through the electrode but once the PZT is exposed. From an acoustics point of view the transducer of FIG. 6b not only has a missing modified electrode portion but the PZT in that selected region is also selectively depoled or reduced in poling level by heating toward the known Curie temperature of particular PZT formulations. The acoustic difference between the modified structures of FIGS. 6a and 6b is that in the FIG. 6a structure, since the PZT in the HA area is still poled, one can have fringing electrical fields from remaining adjacent electrode still firing the PZT to some degree. In the case of FIG. 6b because the poling in the region HA has been reduced, possibly to zero, the fringing fields are unable to excite the PZT in the region of HA. This difference is small in the overall spectrum of transducer 2 unless one has a significant number or area of modified regions.

Figure 6C:
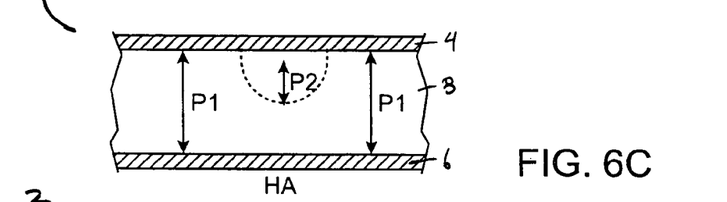

Moving now to FIG. 6c we see the case wherein a thermally-based laser has heated the electrode in the HA region which, in turn or in parallel, heats the underlying PZT in the HA region. In this case the heating is insufficient to ablate the electrode but is high enough to locally depole the PZT to reduced poling P2 in the region HA.

Figure 6D:
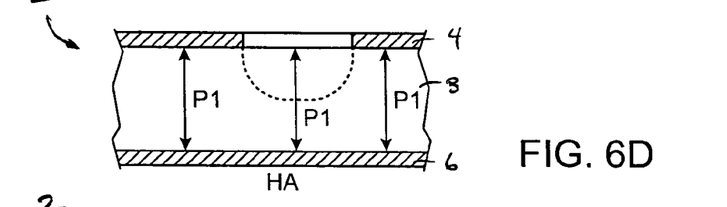

FIG. 6d shows a transducer 2 for the case wherein a laser ablates and removes the electrode at region HA and provides modest nonzero heating to the PZT however that heating is below the Curie temperature so the poling remains at the original P1 level.

Figure 6E:
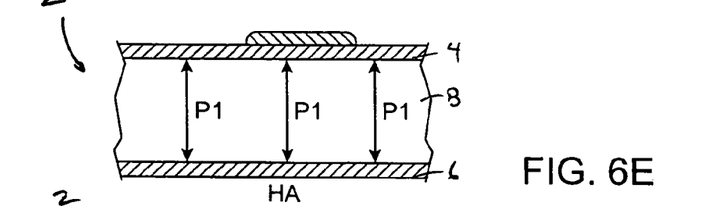

FIG. 6e shows a transducer 2 wherein in the general HA hotspot region we have deposited a small mass of material on the electrode 6e. Adding mass will provide a mass-loading downshift of the local frequency spectra. This spectral contribution change will be superimposed on the overall transducer 2 spectrum. Thus such mass-loading may be implemented in order to beneficially affect not only the local spectral contribution but the overall integrated spectrum.

Figure 6F:
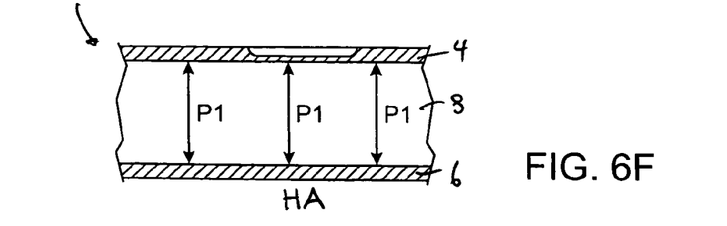

FIG. 6f shows a transducer wherein mass has been removed from the electrode in a hotspot region HA. The mass removal has two effects. The first is a frequency upshift opposite that of FIG. 6e. The second is that the electrode becomes more resistive in the HA region thus delivering a slightly lower voltage pulse. Included in the scope of the invention is the case wherein the modification means, such as a thermal laser, heats an electrode an either increases or decreases its local resistivity in order to affect the applied local voltage pulse.

We have repeatedly referred to HA as a hotspot as an illustrative deviation from a desired activity level at that location. We emphasize now that the deviation being mapped and modified can be any deviation of any one or more acoustic or electro-acoustic parameters which affect the acoustic performance in transmit or receive operation. We emphasized as illustrative examples electrode removal and PZT depoling. Other variables that are known to be influenced by such localized electrode and/or piezomaterial modifications include PZT Kt and capacitance as well as crystallographic stiffnesses and coupling coefficients. We also show our transducer as a monolithic transducer 2. The scope of the invention also covers the cases where the transducer is of a composite or multi-element nature. The activity being modified may be any acoustic or electroacoustic activity such as an acoustic intensity, an acoustic frequency spectrum, an acoustic coupling coefficient, a degree or state of poling, an electroacoustic loss factor or coupling coefficient, a phase of an acoustic wave, a mass or dimension of an acoustic component which affects mass-loading, a resonant behavior or a degree of narrow or broad bandedness for example. Any one or more passive or active materials that is part of the transducer or is in the acoustic path forwards or backwards may be so modified. It will also be realized from figures such as FIGS. 6b and 6c that the PZT properties are actually rendered nonuniform in the thickness dimension despite the fact that the example modification means address the materials from only one face.

Thus, it can be appreciated that the modification of activity across the transducer 2 may be accomplished in a number of different ways. Of course, various methods and devices described herein may be used together to modify the characteristics of the transducer.

After modification of the transducer 2, the transducer 2 may be retested to determine whether any areas still do not meet the threshold criteria and/or to validate the modification(s) made. If parts of the ultrasound transducer 2 still do not meet the maximum deviation criteria the ultrasound transducer 2 may be modified further and retested as necessary. After modification of the ultrasound transducer 2, parts of the ultrasound transducer 2 may be selectively repaired or restored after being modified. An example of this would be wherein an electrode was locally removed in order to locally depole the PZT but the manufacturer desires to replace the missing electrode simply to chemically protect the depoled PZT in that modified region.

It will be understood that one may optionally conduct mapping and modification operations in parallel on a given transducer—and perhaps even two or more of mapping, modification, and remap validation. Such decisions will preferably be limited only by the physical interference of the mapping and modification hardware.

It will also be understood that we have shown in our examples the transducer under test being fired at a low power in air. One may also choose to fire the transducer into water or into a phantom. In such a case one could map from the PZT exposed backside using thermography or from the transducer frontside using hydrophones or Schlieren imaging, for example, and modify in-place or after moving to a separate station. Certain acoustic behaviors and thermal behaviors, particularly if they are of a nonlinear nature, may best be seen using full power testing. Thus the invention is not limited to testing at low power and inferring high power behavior.

We have mentioned that the invention may be applied to transducers coupled to acoustic standoffs or spacers widely known to the acoustic arts. Such standoffs are frequently used to implement skin cooling, to implement disposable standoff sanitary skin-contact schemes, or to move the acoustic focus back toward the skin surface. The modification means of the invention may be used, for example, to modify the passive acoustic attenuation of the standoff material to reduce hotspots at the focal region-even if the focal hotspot is caused by a hotspot on the transducer face its negative consequence can be modified by a downstream prefocal propagation modification.

The present invention has been described in connection with various preferred embodiments, however, it is understood that various modifications may be made without departing from the scope of the invention. Furthermore, the present invention may be applied to a wide variety of acoustic producing devices including piezoacoustic, magnetoacoustic, electroacoustic, thermoacoustic, optoacoustic and micromechanical ones and is not limited to those discussed, described or suggested herein.

What is claimed is:

1. A method of manufacturing an ultrasound transducer, comprising:
   providing an ultrasound transducer;
   activating the ultrasound transducer;
   sensing an activity of the ultrasound transducer other than frequency;
   detecting a location on the ultrasound transducer which does not meet an acceptance criteria; and
   modifying at least part of the ultrasound transducer to modify the activity at the location which does not meet the acceptance criteria.

2. The method of claim 1, wherein
the detecting step is carried out by determining whether the activity at the location exceeds a threshold level of activity; and
the modifying step is carried out to reduce the activity at the location.
3. The method of claim 1, wherein
the sensing step is carried out by sensing the activity across an area of the ultrasound transducer.
4. The method of claim 3, wherein
the sensing step is carried out indirectly by sensing the activity in an ultrasound beam path created by the ultrasound transducer during the activating step.
5. The method of claim 3, wherein
the sensing step is carried out across an active area of the ultrasound transducer.
6. The method of claim 1, further comprising
sensing the activity of the ultrasound transducer after the modifying step.
7. The method of claim 1, further comprising
mounting the ultrasound transducer to a medical device, the medical device being configured to ablate tissue.
8. The method of claim 1, wherein
the providing step is carried out with the ultrasound transducer producing a focused ultrasound beam having a focal length less than 12 mm.
9. The method of claim 1, wherein
the modifying step includes a step of removing material from the ultrasound transducer.
10. The method of claim 9, wherein
the step of removing material is carried out with a laser.
11. The method of claim 1, wherein
the sensing step is carried out with the activity being at least one of a temperature and an acoustic output parameter.
12. The method of claim 1, wherein
the sensing step is carried out by measuring temperature across an area of the ultrasound transducer.
13. The method of claim 1, further comprising
saving a map of the ultrasound transducer activity from the sensing step;
the modifying step being carried out using the map.
14. The method of claim 1, wherein
the activating step is carried out by directing acoustic energy at the transducer;
the sensing step being carried out by sensing electrical impulses created by the transducer resulting from the acoustic energy.
15. The method of claim 1, wherein
the modifying step is carried out with a laser being selected from the group of lasers consisting of UV lasers and excimer lasers.
16. The method of claim 1, wherein
the providing step is carried out with the ultrasound transducer having an active electrode, a ground electrode and a piezoelectric layer.
17. The method of claim 1, further comprising
mounting a membrane over an active face, the membrane being adapted to hold a fluid between the active face and the membrane, the membrane also forming a contact surface which contacts the tissue being treated.
18. The method of claim 17, wherein
the modifying step is carried out by depoling at least part of the piezoelectric material.
19. The method of claim 1, wherein
the sensing step is carried out by sensing the activity on a first side of the ultrasound transducer; and
the modifying step is carried out by modifying a second side of the ultrasound transducer which is opposite the first side of the ultrasound transducer.
20. The method of claim 1, wherein
the sensing step is carried out by sensing the activity on a first side of the ultrasound transducer; and
the modifying step is carried out by modifying the first side of the ultrasound transducer.
21. The method of claim 1, wherein
the modifying step is carried out by changing a shape of the ultrasound transducer to modify the activity level at the location which does not meet the acceptance criteria.
22. The method of claim 1, wherein
the modifying step is carried out by changing a mass of the ultrasound transducer to reduce the activity level at the location exceeding the acceptance criteria.
23. The method of claim 1, wherein
the modifying step is carried out by modifying a poling of a part of the ultrasound transducer.
24. The method of claim 1, wherein
the modifying step is carried out by adding material to the ultrasound transducer.
25. The method of claim 1, further comprising
adding a matching layer to the ultrasound transducer after the modifying step.
26. The method of claim 1, further comprising
retesting the ultrasound transducer after the modifying step by repeating the activating, sensing and detecting steps.
27. The method according to claim 1, wherein the sensed activity is selected from the group consisting of acoustic intensity output, acoustic-receive sensitivity, and acoustically output-derived waste-heat.

* * * * *